United States Patent [19]
Yarnall et al.

[11] Patent Number: 5,491,737
[45] Date of Patent: Feb. 13, 1996

[54] MATERIAL HANDLING AND INSPECTION APPARATUS AND METHOD

[75] Inventors: Ransom A. Yarnall, La Mesa; J. Paul Axford; Dale D. Thayer, both of San Diego, all of Calif.

[73] Assignee: ThermoSpectra Corporation, Franklin, Mass.

[21] Appl. No.: 299,928

[22] Filed: Aug. 31, 1994

[51] Int. Cl.⁶ .......................... G01N 23/02; G01B 15/06
[52] U.S. Cl. .............................. 378/58; 378/69; 414/146
[58] Field of Search .................... 378/58, 68, 69; 414/146, 154, 172, 586

[56] References Cited

U.S. PATENT DOCUMENTS

| | | | |
|---|---|---|---|
| 4,511,918 | 4/1985 | Lemelson | 358/107 |
| 5,000,655 | 3/1991 | Pate | 414/788.8 |
| 5,351,078 | 9/1994 | Lemelson | 348/135 |

OTHER PUBLICATIONS

"CXI-3600, In-Line Process Monitor," IRT Corporation, 1993.
"Flexible Edge Handling Systems," Flexible Technologies, Inc. No Date.
"The Bosch AutoRail-1 System for modular printed circuit board handling," Bosch Automation Products, 1990.
"Boardflo Conveyor Systems," Applied Conveyor Engineering Division of Universal Instruments Corporation, 1990.

Primary Examiner—David P. Porta
Assistant Examiner—David Vernon Bruce
Attorney, Agent, or Firm—Willian Brinks Hofer Gilson & Lione

[57] ABSTRACT

According to the present invention, a material handling system for transporting a device to or from a radiation chamber in which the device is inspected is provided. The system includes a shuttle carriage having a base and two opposing walls, a conveyor mounted between the two opposing walls of the shuttle carriage, and means for moving the shuttle carriage along a path between a loading position and an unloading position. The system also includes a housing that encloses the shuttle carriage and the moving means. The housing has an internal cavity that is fitted to the two opposing walls. The housing also has a first opening coincident with the loading position and a second opening coincident with the unloading position. Further, a drive mechanism is provided for extending the conveyor partially through the first opening and the second opening.

10 Claims, 9 Drawing Sheets

MATERIAL HANDLING AND INSPECTION APPARATUS AND METHOD

BACKGROUND OF THE INVENTION

The present invention relates to a material handling and inspection apparatus and method, and more particularly, to an apparatus and method for handling and inspecting a series of devices carried by a moving conveyor.

In the production environment, it is becoming increasingly difficult to achieve satisfactory process control using visual inspection techniques. This is particularly true when the devices being produced are of a size or complexity that makes visual inspection time consuming, and cost prohibitive if not impossible. For example, printed circuit boards having thousands of electrical connections are now commonplace. Frequently, many of these electrical connections cannot be visually inspected because they are located below components attached to the printed circuit board. Even if all the electrical connections could be visually inspected, time and cost constraints may require that only sample printed circuit boards be inspected, rather than each printed circuit board. However, sample inspections may be insufficient to achieve satisfactory process control.

Inspection time for complex devices, such as printed circuit boards, may be greatly reduced through automated inspection. An automated apparatus for determining the quality of solder connections on printed circuit boards is shown in U.S. Pat. No. 4,809,308. This apparatus utilizes x-rays to inspect solder quality on circuit boards that are loaded onto a motion table. Because an operator may load the printed circuit boards, the apparatus includes safety interlocks to prevent leakage of radiation. Although the automated apparatus greatly reduces inspection time compared to visual inspection, it is desirable to minimize inspection time, while maintaining safety, so that the inspection can be performed at production line rates, even for complex devices.

Accordingly, it could be desirable to have an improved material handling and inspection apparatus.

SUMMARY OF THE INVENTION

According to a first aspect of the invention, a material handling system for transporting a device to or from a radiation chamber in which the device is inspected is provided. The system includes a shuttle carriage having a base and two opposing walls, a conveyor mounted between the two opposing walls of the shuttle carriage, and means for moving the shuttle carriage along a path between a loading position and an unloading position. The system also includes a housing that encloses the shuttle carriage and the moving means. The housing has an internal cavity that is shaped to mate with the two opposing walls. The housing also has a first opening coincident with the loading position and a second opening coincident with the unloading position.

According to a second aspect of the invention, a method of inspecting a series of devices is provided. The method includes the steps of conveying a first device with a first conveyor to an input shuttle assembly positioned adjacent to the first conveyor, shuttling the first device with the input shuttle assembly through a housing to an inspection apparatus, loading the first device from the input shuttle assembly to the inspection apparatus, and simultaneously inspecting the first device and returning the input shuttle assembly to the position adjacent to the first conveyor. The method further includes the steps of conveying a second device with the first conveyor to the input shuttle assembly, shuttling the second device with the input shuttle assembly to the inspection apparatus, unloading the first device from the inspection apparatus to an output shuttle assembly, loading the second device from the input shuttle assembly to the inspection apparatus, and simultaneously inspecting the second device and returning the input shuttle assembly to the position adjacent to the first conveyor. Next, the method includes the steps of shuttling the first device with the output shuttle assembly to a second conveyor.

According to a third aspect of the invention, a material handling system for transporting a device through an inspection apparatus is provided. The material handling system includes a first conveyor, and an input shuttle assembly positioned between the first conveyor and the inspection device. The input shuttle assembly transfers the device from the first conveyor to the inspection apparatus. The system also includes a second conveyor, and an output shuttle assembly positioned between the inspection apparatus and the second conveyor. The output shuttle assembly transfers the device from the inspection apparatus to the second conveyor.

DETAILED DESCRIPTION OF THE PRESENTLY PREFERRED EMBODIMENT

Figure 1:
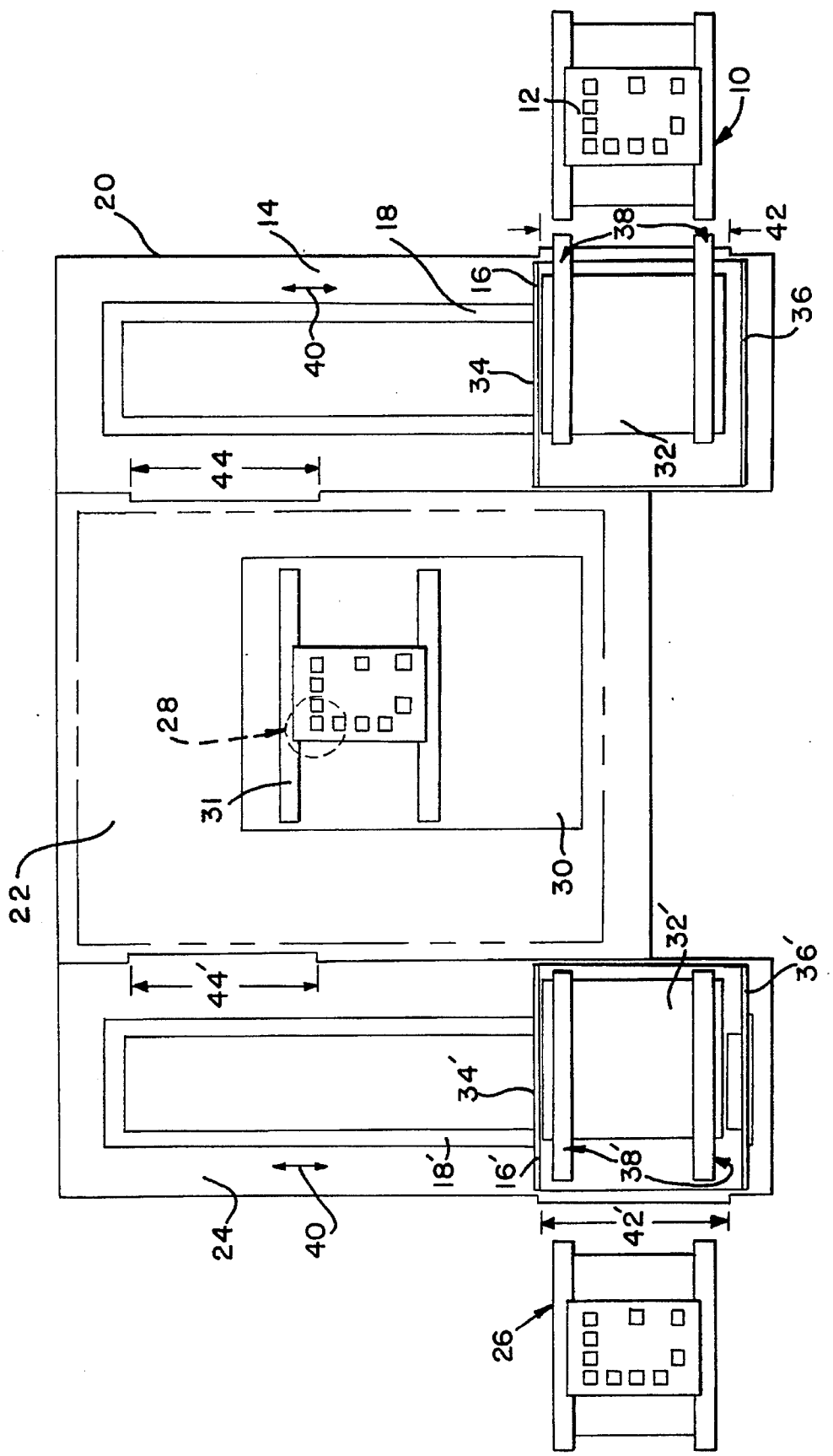
FIG. 1 is a schematic diagram of a material handling and inspection apparatus in accordance with the present invention.

Reference is now made to FIGS. 1 through 7 in which like elements are referred to by like numerals. FIG. 1 is a schematic diagram of a material handling and inspection apparatus in accordance with the present invention. An input conveyor 10 is shown carrying a device 12 to be inspected. An input shuttle assembly 14 is located adjacent to an end of the input conveyor 10. The input shuttle assembly 14 has a shuttle carriage 16 that is slidably mounted upon a linear bearing assembly 18 within a housing 20. An inspection apparatus 22 is attached to the input shuttle assembly 14. An output shuttle assembly 14', which has like components to the input shuttle assembly 14, is attached to the opposite side of the inspection apparatus 22 from input shuttle assembly 14. The components of the output shuttle assembly 14' are designated with a prime following the corresponding numeral from the input shuttle assembly 14 in order to distinguish the components of the output shuttle assembly 14' from the components of the input shuttle assembly 14. An output conveyor 26 is located adjacent to the output shuttle assembly 14'.

The inspection apparatus 22 is preferably an automated, real-time x-ray imaging apparatus, which includes an x-ray source 28, an x-y table 30, and an inspection conveyor 31 mounted to the x-y table 30, such as the models MV6000 and CXI-3600 manufactured by IRT Corporation of San Diego, Calif. for performing circuit board solder quality inspection. Alternatively, the inspection apparatus 22 may be any type of inspection device that utilizes a source of penetrating radiation. An appropriate clamping mechanism is provided to secure the device 12 for movement about the x-y table 30 as the x-y table 30 moves during inspections. Preferably, the clamping mechanism is pneumatically controlled to project into the conveyor belt, whereby the device 12 will be clamped between the conveyor belt and a rigid material block. Each of the conveyors 38, 38' and 31 may be motor driven.

As shown in FIG. 1, the shuttle carriage 16 has a base 32 and two opposing walls 34 and 36. A shuttle conveyor 38 is mounted to the base 32 between the opposing walls 34 and 36. The shuttle conveyor 38 is preferably mounted to the base 32 in a manner that allows the shuttle conveyor 38 to be partially extended from the shuttle carriage 16 between the opposing walls 34 and 36, as is further described below.

Figure 2:
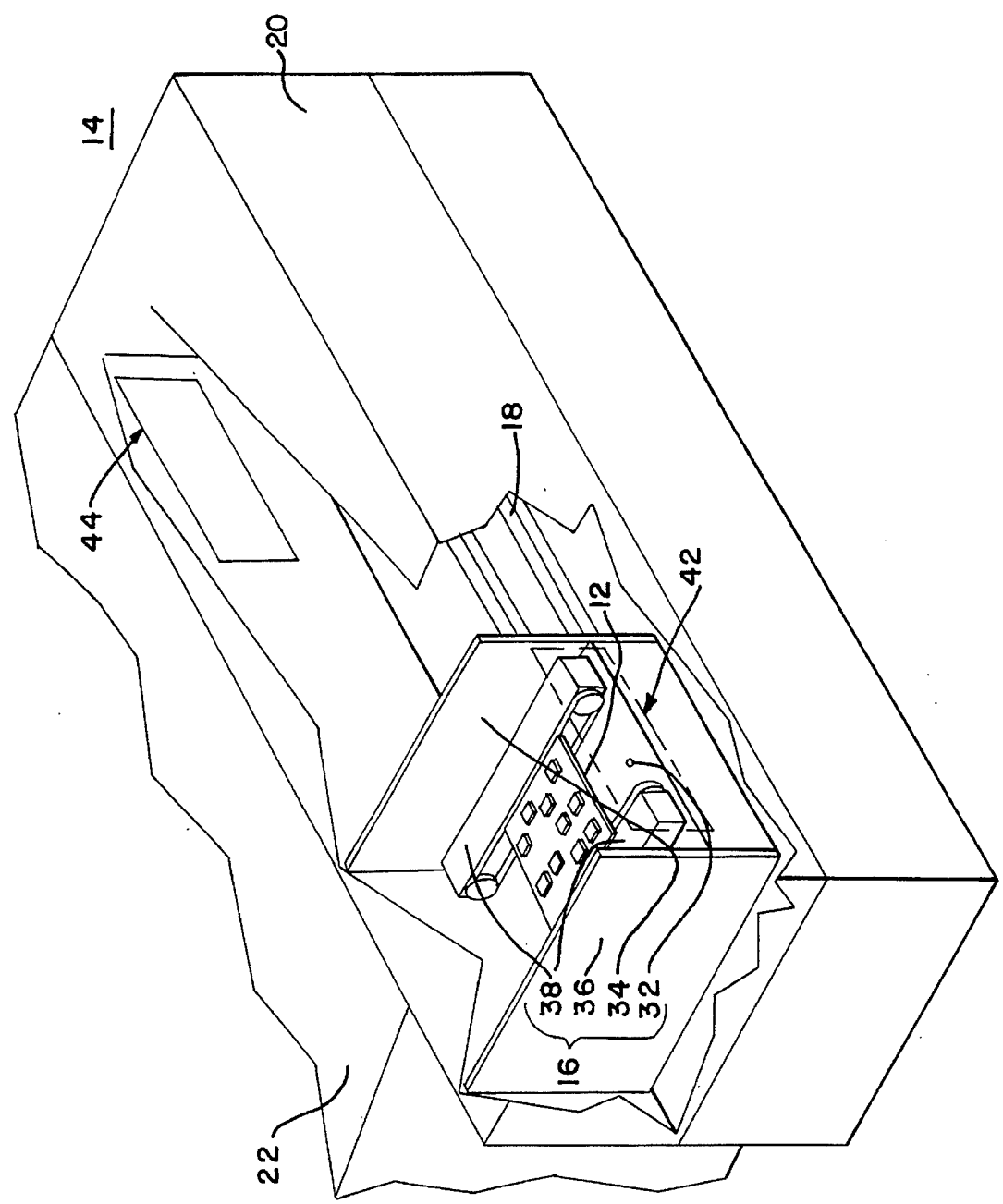
FIG. 2 is a cut-away isometric view of an input shuttle assembly for the material handling and inspection apparatus of FIG. 1.

FIG. 2 is a cut-away, isometric view of the input shuttle assembly 14 shown in FIG. 1. The housing 20 of the input shuttle assembly 14 has a first opening 42 and a second opening 44. The first opening 42 and the second opening 44 in the housing 20 are large enough to pass the shuttle conveyor 38 and the device 12. However, the length of the openings 42 and 44 is shorter than the distance between the opposing walls 34 and 36 of the shuttle carriage 16.

Preferably, the walls 34 and 36 and the housing 20 are constructed from sheet steel. In addition, those portions of the inspection apparatus 22 and the housing 20 that are within the direct line-of-sight of the x-ray source 28 are preferably lined with 3/16" thick lead sheets. The inner surface of the shuttle carriage 16 is also preferably lined with 1/16" thick lead. Although it is not necessary that the periphery of the walls 34 and 36 contact the inner surface of the housing 20, any gap between the walls 34 and 36 and the housing 20 is preferably small enough to eliminate all direct paths between the x-ray source 28 and the exterior of the housing 20.

Figure 3:
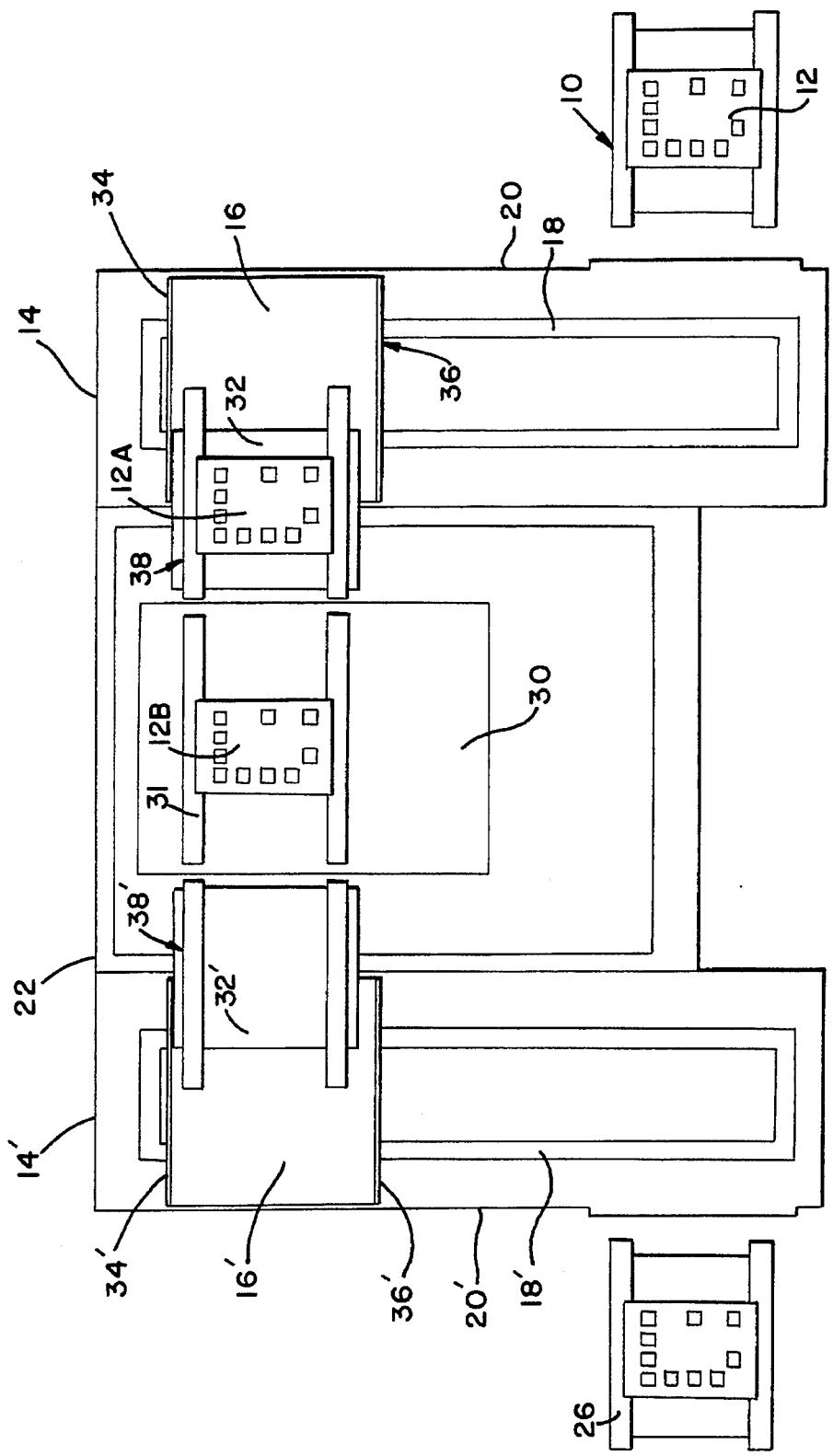
FIG. 3 is a schematic diagram of the material handling and inspection apparatus of FIG. 1 in which an input shuttle conveyor and an output shuttle conveyor are illustrated in their extended positions toward an x-y table.

As shown in FIG. 3, the shuttle conveyors 38 and 38' are preferably mounted to the bases 32 and 32' of the shuttle carriages 16 and 16' in a manner that allows the shuttle conveyors 38 and 38' to be extended partially through the first openings 42, 42' and the second openings 44, 44'. In FIG. 3, the shuttle conveyors 38 and 38' are illustrated extended through the second openings 44 and 44'. In this position, the devices 12A and 12B may be transferred simultaneously to the inspection conveyor 31 and to the output shuttle conveyor 38', respectively.

Figure 5A:
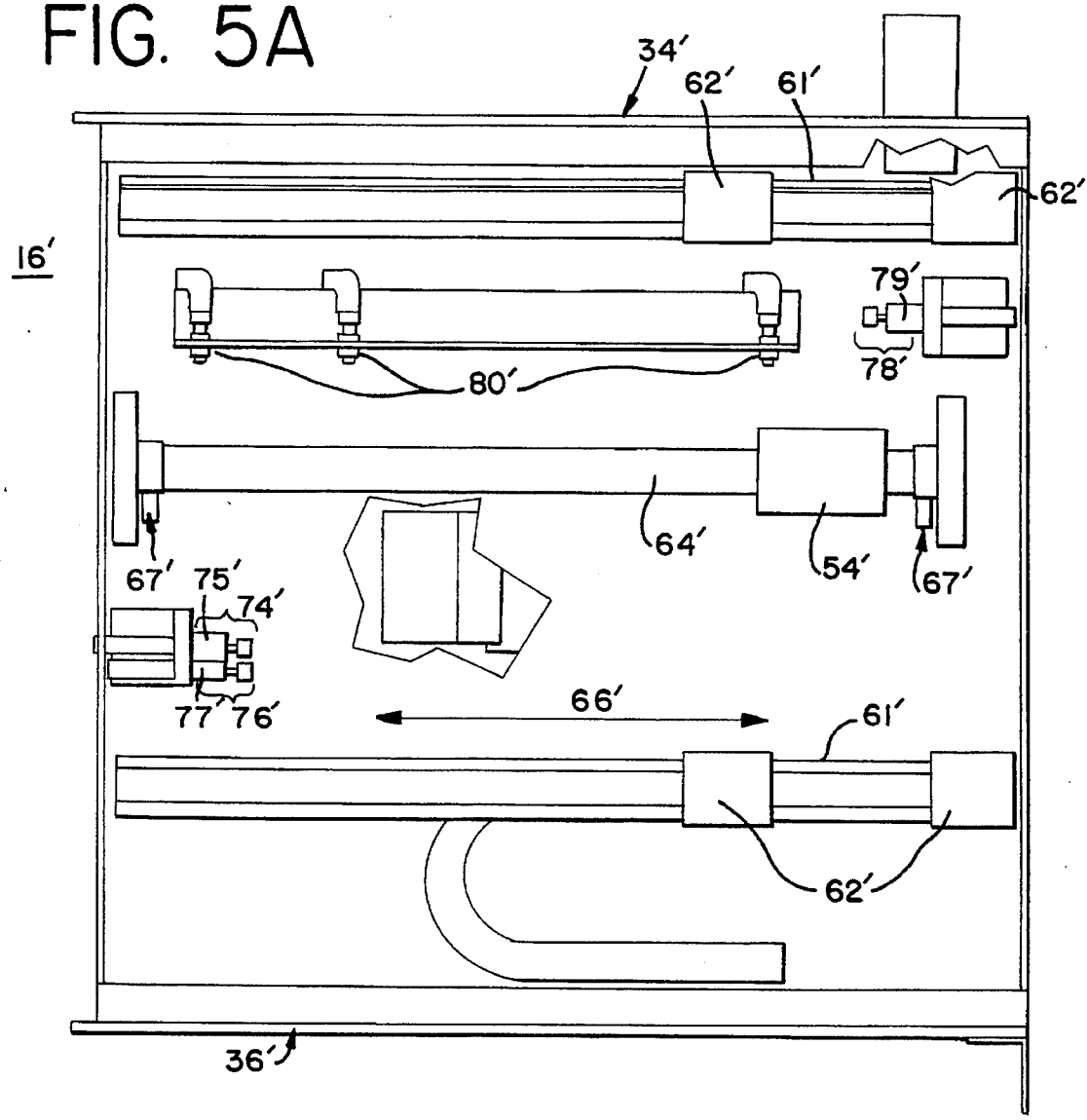
FIG. 5A is a sectional view of an output shuttle carriage in accordance with the present invention.

FIG. 5A is a sectional view of the output shuttle carriage 16' in which the base 32' and the output shuttle conveyor 38' have been removed. The corresponding elements of the input shuttle carriage 16 are arranged as the mirror image of FIG. 5A. A linear bearing assembly 60', including two linear trackways 61' and four linear bearing blocks 62', is mounted within the shuttle carriage 16'. Preferably, a pneumatic rodless cylinder 64' is arranged to drive the shuttle conveyor 38' in the directions of the double arrow 66'. A source 70 of compressed gas is coupled to a fitting 67' at each end of the cylinder 64' through a pneumatic valve 90.

Figure 5B:
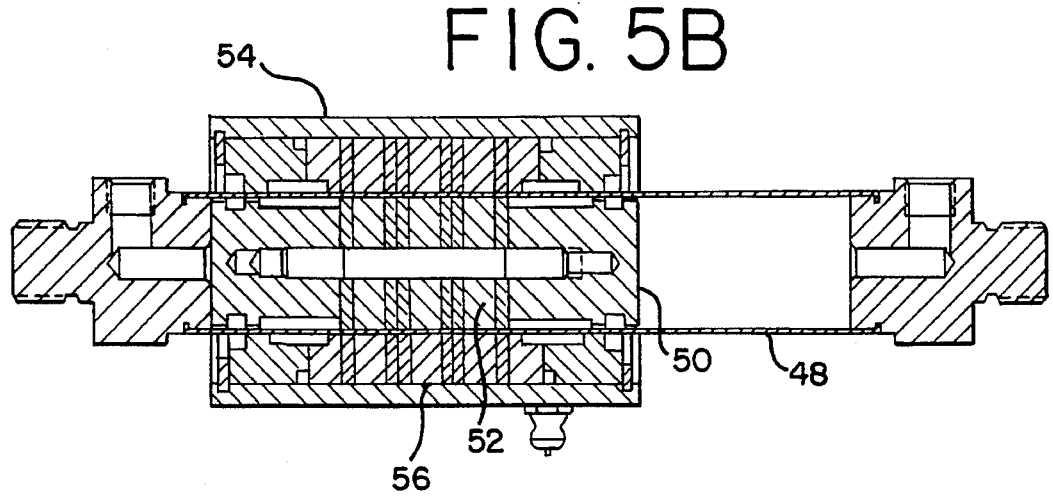
FIG. 5B is a sectional view of a pneumatic rodless cylinder and cylinder carriage in accordance with the present invention.

A suitable commercially available pneumatic cylinder for this application is the Ultran rodless cylinder from Bimba of Monee, Ill., which is shown in FIG. 5B. The Ultran rodless cylinder has a section of stainless steel tubing 48' that contains a piston 50'. A number of magnets 52' are located on the piston 50'. A cylinder carriage 54' is slidably mounted on the tubing 48', and a number of magnets 56' are also located on the cylinder carriage 54'. The magnets 52' and the magnets 56' magnetically couple the piston 50' to the cylinder carriage 54'.

Returning to FIG. 5A, the cylinder carriage 54' and the four linear bearing blocks 62' are attached to the base 32' (not shown in FIG. 5A) so that the travel of the shuttle conveyor 38' may be driven by the pneumatic rodless cylinder 64'. Preferably, three mechanical stops, a left stop 74', a home stop 76', and a right stop 78', are attached to the shuttle carriage 16' to limit the travel of the shuttle conveyor 38'. At the home stop 76' position, the shuttle conveyor 38' is contained within the shuttle carriage 16' so that the shuttle carriage 16' may move between the first opening 42' and the second opening 44'. At the left stop 74' position, the shuttle conveyor 38' is extended to the left partially through the first opening 42'. At the right stop 78' position, the shuttle conveyor is extended to the right partially through the second opening 44'.

Figure 5D:
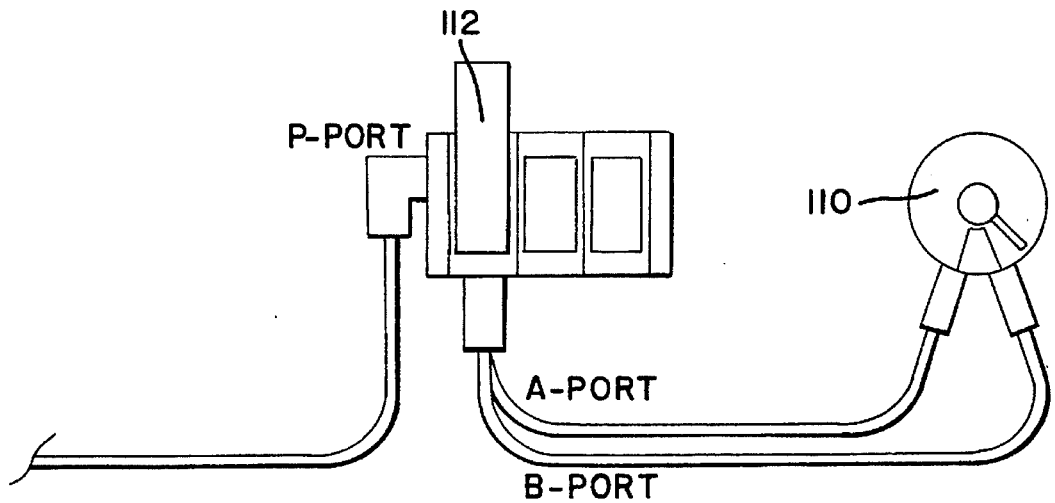
FIG. 5D is a schematic diagram of control system for a stop mechanism for use with a conveyor in the shuttle carriage or inspection apparatus.

As shown in FIG. 5A, the mechanical stops 74', 76' and 78' are preferably horizontally mounted hydraulic shock absorbers fitted with stop collars 75', 77' and 79', respectively. Appropriate contact blocks may be attached to the bottom side of the base 32' to define the left and right stop positions. In addition, a pneumatic cylinder 86' coupled to a source 70 of compressed gas by a pneumatic valve 92, as shown in FIG. 5C, may be mounted to the left contact block so that, when the rod of the pneumatic cylinder 86' is extended by the application of the compressed gas, the rod will strike the home stop 76' defining the home position.

Alternative stop arrangements may be employed without departing from the scope of the present invention. For example, the left stop 74' and the right stop 78' may be replaced by shock absorbing blocks mounted on or near the rodless cylinder 64' to directly limit the travel of the cylinder carriage 54'. Alternatively, optical or electronic sensors may be used to control the application of the compressed gas to the cylinder 64' to thereby stop the cylinder carriage 54' at the appropriate position.

As shown in FIG. 5A, the shuttle carriage 16' includes three proximity sensors 80', which may be positioned to sense the position of the cylinder carriage 54'. More particularly, the proximity sensors 80' may sense that the cylinder carriage 54', and therefore the shuttle conveyor 38', has reached its left, home or right position. A suitable proximity sensor for this application is manufactured by Omron under the part no. TL-X1R5C2-P1E, which is available from Western Switches & Controls, Inc. of San Diego, Calif. The proximity sensors are coupled to a system controller 88.

Figure 6:
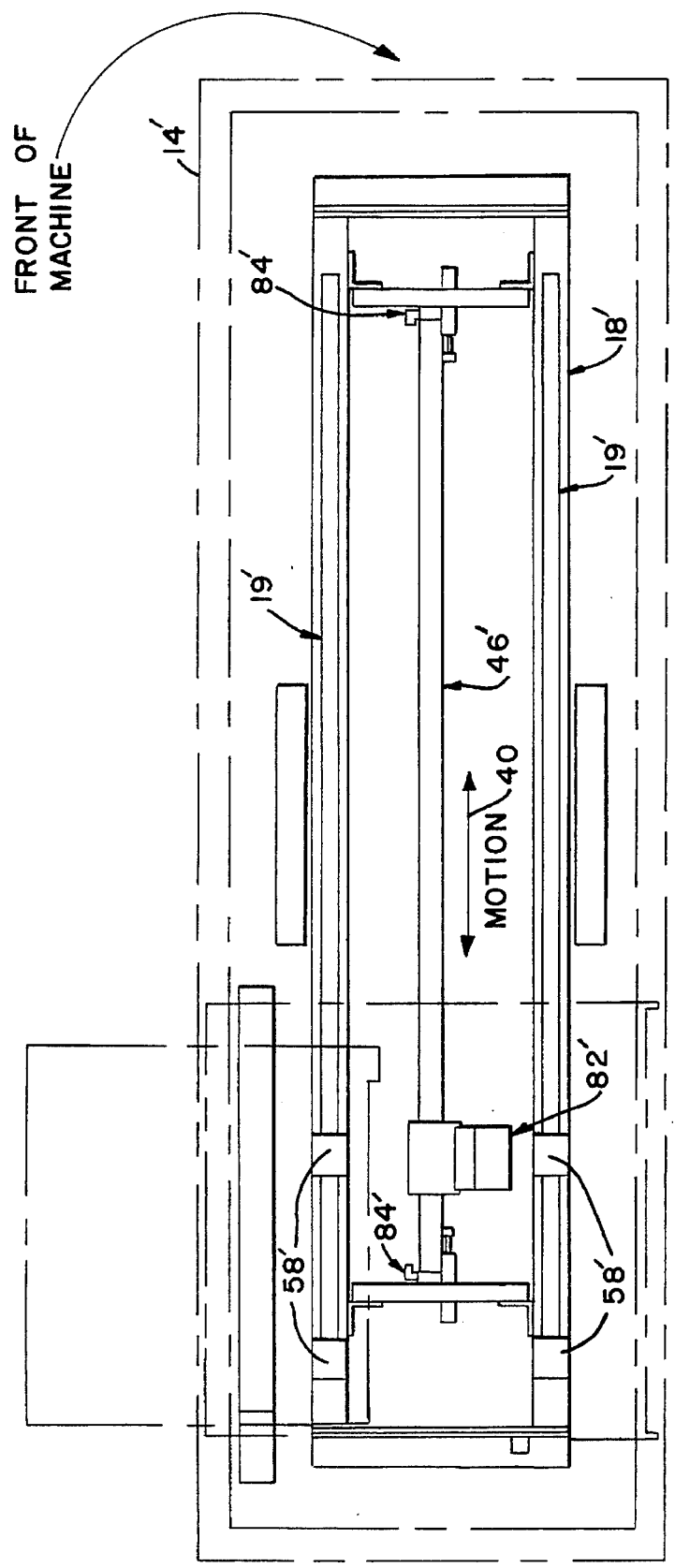
FIG. 6 is a sectional view of an output shuttle assembly in accordance with the present invention.

Referring now to FIG. 6, a sectional view of the output shuttle assembly 14' is shown to illustrate the drive mechanism for the shuttle carriage 16' (not shown). The linear bearing assembly 18' includes two linear trackways 19' and four linear bearing blocks 58'. Mounted between the two linear trackways 19' is a rodless pneumatic cylinder 46', which drives a cylinder carriage 82'. Preferably, the rodless pneumatic cylinder 46' is an Ultran rodless cylinder as shown in FIG. 5B and described above. A source 70 of compressed gas is coupled to each end of the rodless cylinder 46' by fittings 84'. The shuttle carriage 16' (not shown) is mounted to the four linear bearings 58' and the cylinder carriage 82' for guided travel along the direction of the double arrow 40.

The rodless pneumatic cylinders 46' and 64' and the pneumatic cylinder 86' of the output shuttle assembly 14' may be controlled as shown in FIG. 5C. The source 70 of compressed gas is coupled to three pneumatic valves 90, 92 and 94 mounted on a manifold. Each of the valves has a single pressure regulator 96, 98 and 100 respectively, and a speed control 102, 104 and 106 respectively, which permits control of the speed of the piston of cylinders 64', 86' and 46' by throttling exhaust air. Preferably, the valves are solenoid actuated. A suitable commercially available valve for this application is sold under the MARK 3 name by Numatics as model number 031SA4. A suitable commercially available pressure regulator for this application is sold under the MARK 3 name by Numatics as model number 031RS7020. A suitable commercially available speed control for this application is sold under the MARK 3 name by Numatics as kit no. 229-527A.

The valves 90, 92 and 94 may be controlled by the system controller 88. The source 70 of compressed gas is selectively coupled through the valves 90, 92 and 94 each end of the pneumatic cylinders 64', 46' and 86', as shown in FIG. 5C. Thus, the piston 50 and the cylinder carriage 54 may be driven in either direction along the tubing 48 by coupling the compressed gas to the appropriate end of the tubing 48. A like three valve assembly, coupled to the system controller 88, controls the three pneumatic cylinders for the input shuttle assembly 14.

Alternatively, the shuttle carriage 16 may be driven by a conventional pneumatic cylinder having a piston and a rod, although such an arrangement would require a longer pneumatic cylinder to achieve the same travel stroke as the rodless cylinder described above. In addition, the shuttle carriage 16 may alternatively be driven by a motor-driven lead screw. Furthermore, the shuttle carriage 16 may be propelled by other known devices, such as a motor-driven chain, cable, or belt.

Figure 5E:
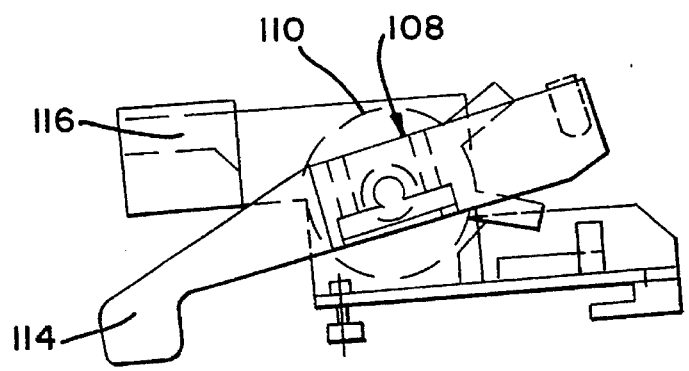
FIG. 5E is a side view of the stop mechanism axially mounted to a rotary actuator.
Figure 5C:
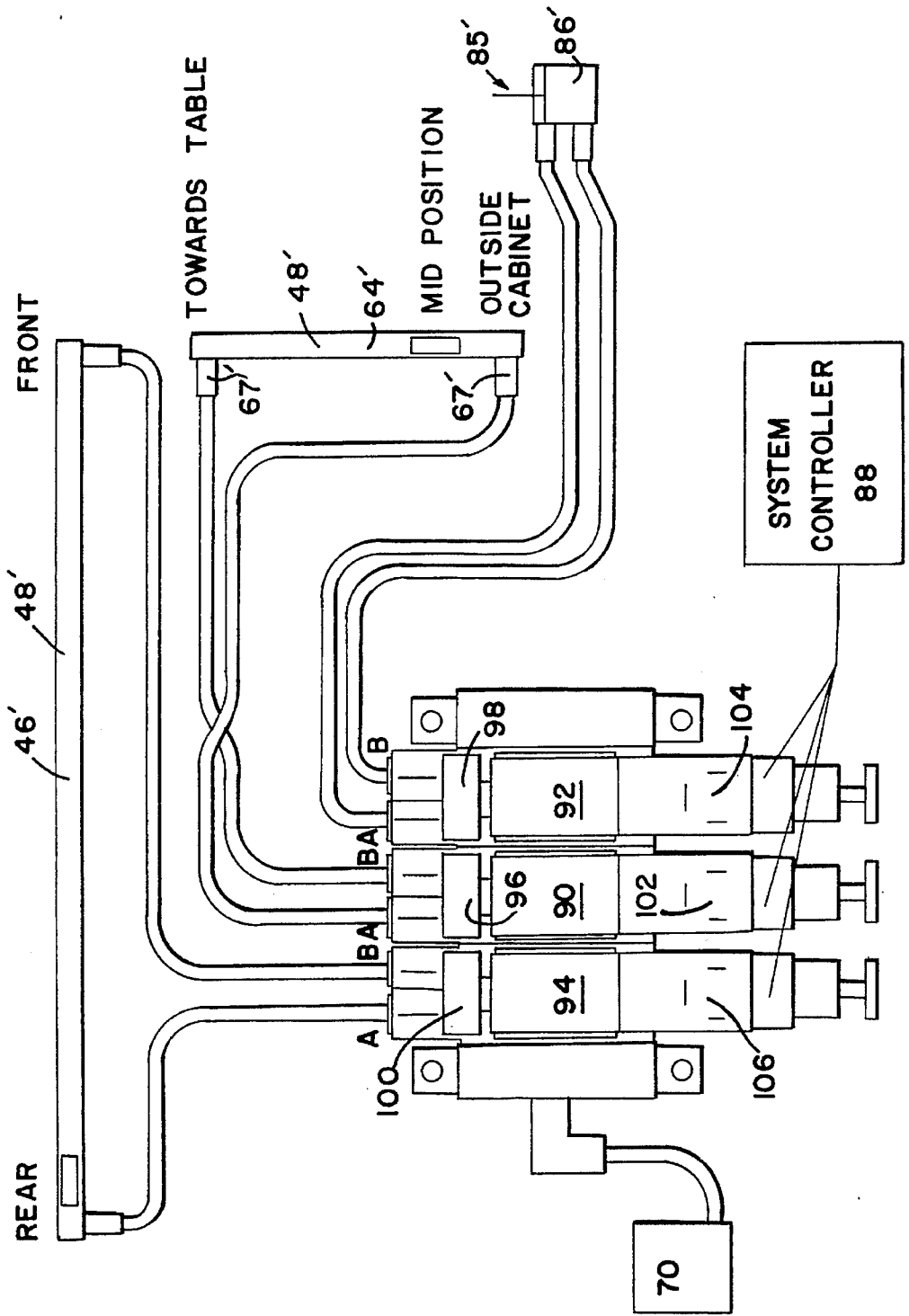
FIG. 5C is a schematic of a pneumatic system for controlling pneumatic cylinders within the shuttle carriage of FIG. 5A.

Each of the shuttle conveyors 38 and 38' and the inspection conveyor 31 is fitted with a device stop mechanism 108, as shown in FIG. 5E, which stops the conveyor when the device 12 has reached the desired location on the conveyor. Preferably, the device stop mechanism 108 is pneumatically controlled, although other electrical or optical sensors, or mechanical stops, could alternatively be used.

FIG. 5D is a schematic diagram of the pneumatically controlled stop mechanism 108. The stop mechanism 108 includes a rotary actuator 110. The rotary actuator 110 is coupled to a valve 112. The valve 112 is controlled by the system controller 88. The stop mechanism 108, as shown in FIG. 5E, is axially mounted to the rotary actuator 110. When the system controller 88 determines that the conveyor 38, 38' or 31 is ready to receive the device 12, the system controller 88 provides a signal to the valve 112 to change the state of the rotary actuator 110, rotating a finger 114 of the stop mechanism 108 into the path of the device 12. The conveyor 38, 38' or 31 may be started by the system controller 88 simultaneously with or after signalling the valve 112. A photodetector 116 is positioned above the finger 114. When the device 12 reaches the finger 114, the photodetector 116 provides a signal to the system controller 88 to stop the conveyor 38, 38' or 31.

Figure 4:
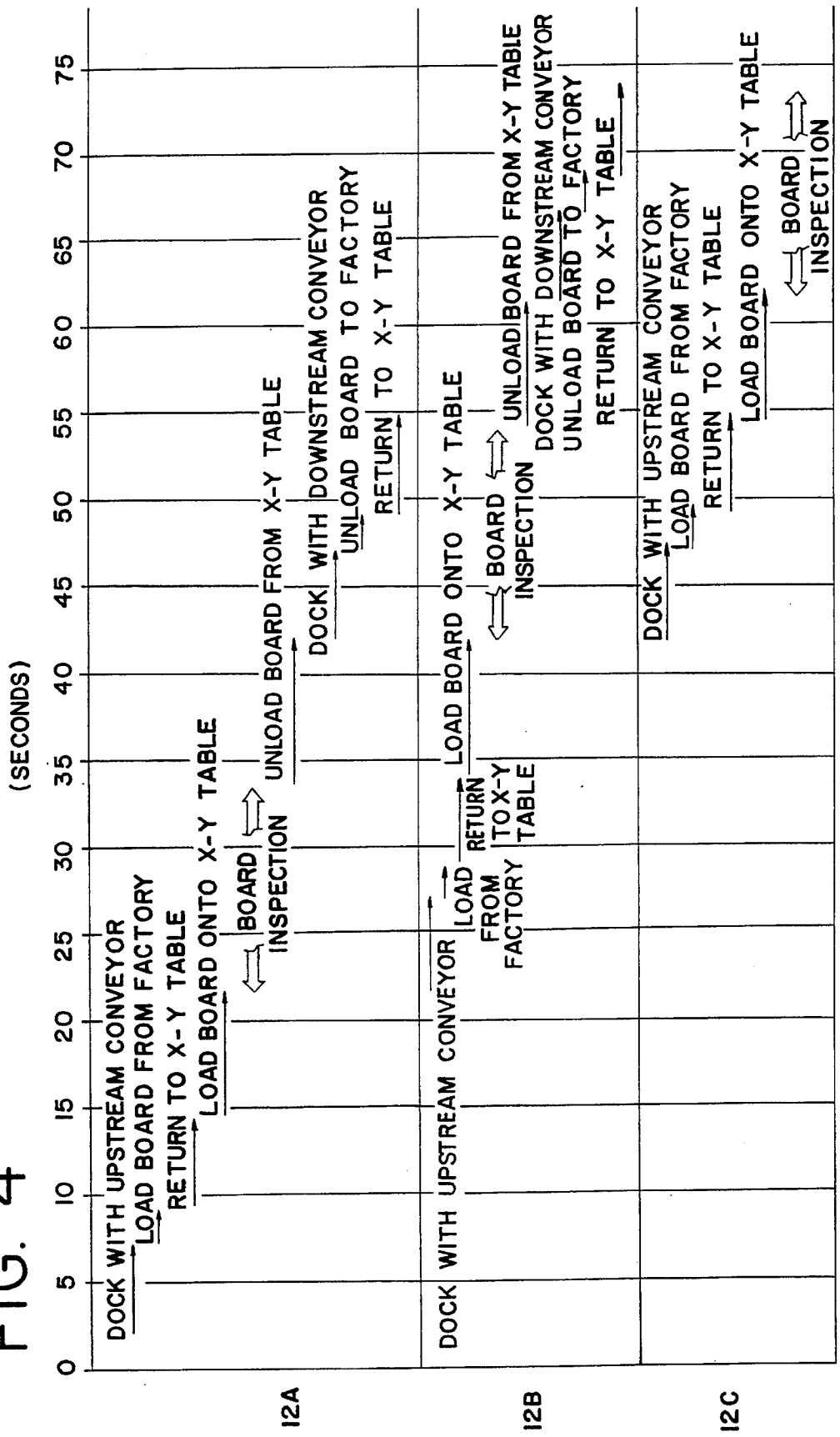
FIG. 4 is a timing diagram for the material handling and inspection apparatus of FIG. 1.

The preferred operation of the material handling and inspection system will now be described with reference to FIGS. 1 and 4 for a series of devices 12. Initially, the shuttle conveyor 38 of the input shuttle assembly 14 is extended partially through the first opening 42, where the shuttle conveyor 38 docks with the input conveyor 10. A first device 12A is loaded from the input conveyor 10 to the shuttle conveyor 38. The shuttle conveyor 38 is retracted into the shuttle carriage 16, which then travels through the housing 20 to the second opening 44. At the second opening 44, the shuttle conveyor 38 is extended into the inspection apparatus 22, where the shuttle conveyor 38 docks with the inspection conveyor 31. Next, the device 12A is loaded from the shuttle conveyor 38 to the inspection conveyor 31. The shuttle conveyor 38 is then retracted into the shuttle carriage 16 and the shuttle carriage 16 returns to the first opening 42 to dock with the input conveyor 10 as the device 12A is inspected.

As the inspection of the device 12A continues, a device 12B is loaded from the input conveyor 10 to the extended shuttle conveyor 38, which then retracts into the shuttle carriage 16. The shuttle carriage 16 and the shuttle carriage 16' then travel to the second openings 44 and 44', respectively. Upon completion of the inspection of the device 12A, the shuttle conveyors 38 and 38' dock with the inspection conveyor 31, and the device 12A is loaded from the inspection conveyor 31 to the shuttle conveyor 38' simultaneously with the loading of the device 12B from the shuttle conveyor 38 to the inspection conveyor 31. The shuttle conveyors 38 and 38' are then retracted into the respective shuttle carriages 16 and 16' and the shuttle carriages 16 and 16' return to the first openings 42 and 42' to dock with the input conveyor 10 and the output conveyor 26, respectively, as the device 12B is inspected.

As the inspection of the device 12B continues, a device 12C is loaded from the input conveyor 10 to the extended shuttle conveyor 38 and the device 12A is unloaded from the shuttle conveyor 38' to the output conveyor 26. When interacting with the input conveyor 10 and the output conveyor 26, it is not necessary that the shuttle carriages 16 and 16' move simultaneously. Next, the shuttle conveyors 38 and 38' retract and the shuttle carriages 16 and 16' return to the second openings 44 and 44', respectively. Upon completion of the inspection of the device 12B, the shuttle conveyors 38 and 38' dock with the inspection conveyor 31. The device 12B is then loaded from the inspection conveyor 31 to the shuttle conveyor 38' while the device 12C is simultaneously loaded from the shuttle conveyor 38 to the inspection conveyor 31. The shuttle conveyors 38 and 38' are then retracted into the shuttle carriages 16 and 16', which then return to the first openings 42 and 42' to dock with the input conveyor 10 and the output conveyor 26, respectively. The operation of the material handling and inspection system will continue in like sequence until the last of the series of devices 12 is loaded onto the output conveyor 26.

Figure 7:
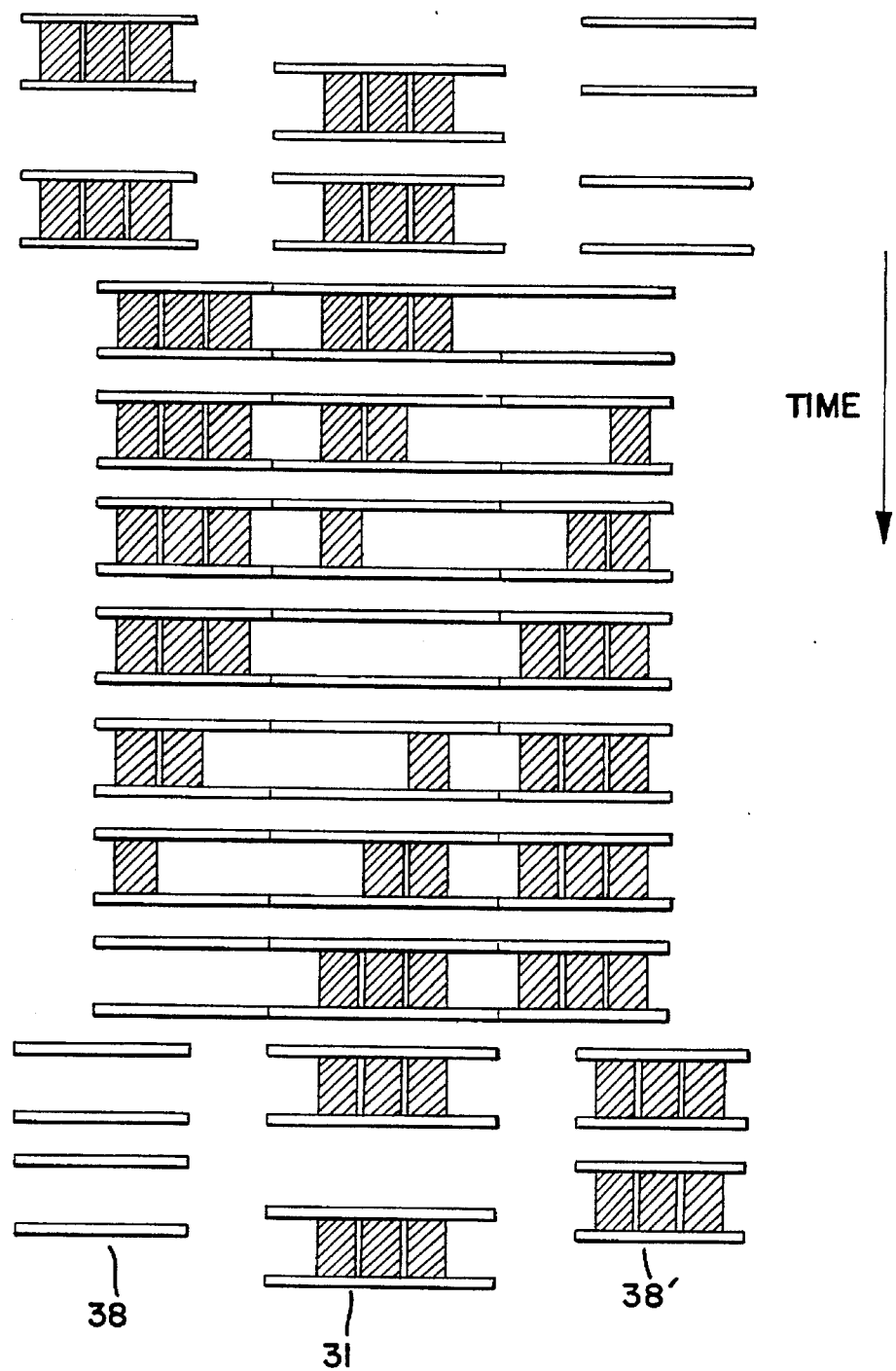
FIG. 7 is a schematic of a load/unload sequence of an inspection conveyor with the shuttle conveyors positioned as shown in FIG. 3, wherein each of the shuttle conveyors and the inspection conveyors is provided with three stop mechanisms.

In an alternative operational mode, more than one device 12 is carried by the shuttle carriages 16 and 16' and the inspection conveyor 31, and is inspected within the inspection apparatus 22 at any one time. For example, as shown in FIG. 7, the shuttle carriage 16 may transport three devices 12B simultaneously and the inspection apparatus 22 may inspect three devices 12A simultaneously. Upon the completion of the inspection routine, the three devices 12A are unloaded onto the shuttle carriage 16' and the three devices 12B are loaded into the inspection apparatus 22. By using three stop mechanisms 108 on each of the shuttle conveyors 38 and 38' and the inspection conveyor 31, and three clamping mechanisms on the inspection conveyor 31, the devices 12 may be loaded into or unloaded from the inspection apparatus 22 one at a time as shown in FIG. 7.

Alternatively, once the shuttle conveyors 38 and 38' and the inspection conveyor 31 are aligned, multiple devices may be simultaneously unloaded from and loaded to the inspection conveyor. Where multiple devices are transported simultaneously, one stop mechanism 108 may be used, rather than three, by locating the stop mechanism 108 to stop the first of the devices 12.

As a further alternative, the stop mechanisms 108 could be replaced by photodetectors. However, at present, the stop mechanism 108 described herein provides a more accurate stop position, which reduces inspection time.

Throughout the operation of the inspection sequence, the travel of the shuttle carriage 16 within the housing 20 is preferably limited so that at least one of the two opposing walls 34 and 36 is located between the first opening 42 and the second opening 44 regardless of the position of the shuttle carriage 16. The opposing walls 34 and 36 are fitted within the inner surface of the housing 20 to prevent leakage of radiation from the x-ray source 28 out of the housing 20. The opposing walls also provide a physical barrier to prevent insertion of any part of the human body through the housing 20 and into the primary x-ray beam from the x-ray source 28. Because of the arrangement of the opposing walls 34 and 36, the need for redundant interlocks is eliminated.

Although the operation of the conveyors 10, 38, 38' and 26 has been described to produce a flow of devices 12 from right to left through the apparatus of FIG. 1, the flow may be reversed, in which case the devices 12 would be loaded from the conveyor 26 and unloaded with the conveyor 10. In addition, the shuttle conveyors 38 and 38' and the inspection conveyor 31 are preferably adjustable in width so that they may accommodate devices 12 of various sizes.

It is intended that the foregoing detailed description be regarded as illustrative rather than limiting and that it is understood that the following claims including all equivalents, are intended to define the scope of the invention.

We claim:

1. A material handling system for transporting a device to or from a radiation chamber in which the device is inspected, comprising:

a shuttle carriage having a base and two opposing walls;

a conveyor mounted between the two opposing walls of the shuttle carriage;

means for moving the shuttle carriage along a path between a loading position and an unloading position; and a housing that encloses the shuttle carriage and the moving means, wherein the housing has an internal cavity that is fitted around the two opposing walls, and wherein the housing has a first opening coincident with the loading position and a second opening coincident with the unloading position.

2. A material handling system as claimed in claim 1, wherein the conveyor is positioned to convey the device in a direction that is transverse to the path between the loading position and the unloading position of the shuttle carriage.

3. A material handling system as claimed in claim 1, further comprising:

a factory conveyor aligned parallel to the conveyor, wherein an end of the factory conveyor is located adjacent to the first opening in the housing.

4. A material handling system as claimed in claim 1, further comprising a radiation cabinet containing an x-y table, wherein the x-y table has a range of motion that allows the x-y table to be positioned adjacent to the second opening in the housing.

5. A material handling system as claimed in claim 1, wherein the conveyor mounted to the shuttle carriage is extensible toward both the first opening and the second opening in the housing.

6. A material handling system as claimed in claim 1, wherein at least one of the two opposing walls is positioned between the first opening and the second opening in the housing.

7. A method of inspecting a series of devices, comprising the steps of:

conveying a first device with a first conveyor to an input shuttle assembly positioned adjacent to the first conveyor;

shuttling the first device with the input shuttle assembly through a housing to an inspection apparatus;

loading the first device from the input shuttle assembly to the inspection apparatus;

simultaneously inspecting the first device and returning the input shuttle assembly to the position adjacent to the first conveyor;

conveying a second device with the first conveyor to the input shuttle assembly;

shuttling the second device with the input shuttle assembly to the inspection apparatus;

unloading the first device from the inspection apparatus to an output shuttle assembly;

loading the second device from the input shuttle assembly to the inspection apparatus;

simultaneously inspecting the second device and returning the input shuttle assembly to the position adjacent to the first conveyor; and shuttling the first device with the output shuttle assembly to a second conveyor.

8. A method of inspecting a series of devices as claimed in claim 7, wherein the step of loading the second device occurs simultaneously with the step of unloading the first device.

9. A method of inspecting a series of devices as claimed in claim 7, wherein inspecting the first device comprises the step of irradiating the first device with a beam of x-rays from an x-ray source.

10. A material handling system for transporting a device through an inspection apparatus comprising:

a first conveyor;

an input shuttle assembly positioned between the first conveyor and the inspection device, wherein the input shuttle assembly transfers the device from the first conveyor to the inspection apparatus;

a second conveyor; and an output shuttle assembly positioned between the inspection apparatus and the second conveyor, wherein the output shuttle assembly transfers the device from the inspection apparatus to the second conveyor.

* * * * *